United States Patent [19]
Johnson et al.

[11] Patent Number: 5,284,483
[45] Date of Patent: Feb. 8, 1994

[54] ACETABULAR CUP INSERTING INSTRUMENT

[75] Inventors: Erin M. Johnson, Warsaw, Ind.; Leroy C. Bayliss, Sherwood, Ohio

[73] Assignee: Zimmer, Inc., Warsaw, Ind.

[21] Appl. No.: 945,558

[22] Filed: Sep. 16, 1992

[51] Int. Cl.5 .................... A61F 5/00; A61F 2/32
[52] U.S. Cl. ............................... 606/86; 606/91
[58] Field of Search .......... 606/86, 87, 88, 89, 606/90, 91; 623/18, 22, 23; 403/256

[56] References Cited

U.S. PATENT DOCUMENTS

| | | | |
|---|---|---|---|
| 4,305,394 | 12/1981 | Bertuch, Jr. | 128/303 R |
| 4,475,549 | 10/1984 | Oh | 128/303 R |
| 4,528,980 | 7/1985 | Kenna | 128/92 EB |
| 4,632,111 | 12/1986 | Roche | 128/303 R |
| 4,716,894 | 1/1988 | Lazzeri | 606/91 |
| 4,911,179 | 3/1990 | Brown | 128/875 |
| 4,993,410 | 2/1991 | Kimsey | 606/100 |
| 5,030,221 | 7/1991 | Buechel | 606/91 |
| 5,037,424 | 8/1991 | Aboczsky | 606/91 |
| 5,116,339 | 5/1992 | Glock | 606/91 |

OTHER PUBLICATIONS

Osteonics Corp.-"Surgical Protocol-Low Profile Threaded Omnifit Cup"-See Figs. 10 and 11 re Cup Driver with Ratchet Assembly-1986.
G. Cremascoli-AN.C.A. Anatomic Ceramic Arthoplasty-See p. 4 re item 8, The Driver Chuck (for Acetabular Cup)-No date available.

Primary Examiner—Michael A. Brown
Attorney, Agent, or Firm—Margaret L. Geringer

[57] ABSTRACT

An acetabular cup inserting instrument includes a first handle and a second handle rotatable about and extending from the first handle. The second handle is ratchetable about the first handle and selectively lockable in a desired position with respect to the first handle. The ratchet mechanism of the second handle includes a biased pawl that engages radially spaced notches on the first handle.

6 Claims, 2 Drawing Sheets

ACETABULAR CUP INSERTING INSTRUMENT

BACKGROUND OF THE INVENTION

The present invention relates to an acetabular cup inserting instrument which is used by a surgeon to insert and properly position an acetabular cup implant into its proper anatomical location.

A number of instruments are known in the art for inserting acetabular cup implants into position in the acetabulum. An example of one such instrument is shown in U.S. Pat. No. 4,716,894 assigned to the assignee of the present invention and incorporated herein by reference. That patent shows a cup inserting instrument with a main gripping handle and second handle which is rotatable about the first handle.

Both the main and second handles of the instrument, shown in U.S. Pat. No. 4,716,894, include grooved, radial disks that intermesh and interlock when a locking sleeve forces the two handles together. The rotatable locking sleeve locks the second handle to the main handle.

Although this instrument enables the second handle to be locked in selectable positions, when the locking sleeve is unlocked thereby disengaging the grooved disks, the second handle can fall unimpeded if it slips out of the surgeon's grasp. Therefore it is important that the surgeon maintain a good grasp on the second handle when in its released position. Free rotatability of the second handle can be prevented to a degree by backing off the locking sleeve to the point where the grooved disks are only partially disengaged. As the second handle is rotated, the teeth on the disks "jump" over each other in much the same fashion as gears that are only partially engaged. However, this jumping movement is very erratic and rough and does not provide the controlled movement that is desirable in order to accurately position the second handle when placing an acetabular cup during a hip replacement procedure.

SUMMARY OF THE INVENTION

The present invention provides a simple, reliable ratcheting mechanism for moving and then locking the second handle into a desired position with respect to the first handle of an acetabular cup positioning instrument of the general type disclosed in U.S. Pat. No. 4,716,894. The acetabular cup inserting instrument of the present invention comprises a first elongated handle with a second elongated handle extending therefrom. The second handle is capable of ratcheting about the longitudinal axis of the first elongated handle. The second handle may be selectively locked in a desired position with respect to the first handle by means of a control knob on the ratcheting mechanism. The instrument aids in properly positioning an acetabular cup in the acetabulum.

An advantage of the present invention is that the second handle rotates smoothly and in a controlled manner about the main handle when not locked thereto. The ratchet mechanism provides a positive engagement at each discrete radial position. In the preferred embodiment, increased accuracy in radially locating the second handle about the main handle is caused by a spring biased pawl carried by one handle engaging detents on the other handle.

Another advantage of the present invention is that the second handle is prevented from swinging freely about the first handle. This increases control of the instrument during positioning of the cup.

An additional advantage of the present invention is that it provides an instrument design which is more compact to increase the surgeon's view of the surgical field. This compact design also enables the instrument to be more lightweight.

A further advantage of the present invention is that the second handle ratchets in both rotational directions. Rotation in both directions permits the surgeon to easily and quickly position the second handle where needed.

Yet another advantage is that when the surgeon makes an adjustment to insert the cup, the surgeon may hold the second handle stationary while rotating the first handle.

The invention, in one form thereof, is an acetabular cup inserting instrument comprising a first elongated handle having a proximal end, a distal end and an intermediate section therebetween, the handle having means on the distal end thereof for attaching to an acetabular cup. A second handle extends from the intermediate section of the first handle and is rotatable about the first handle. A ratchet mechanism yieldably retains the second handle in a plurality of discrete angular positions as the second handle is rotated about the first handle. There is also provided a locking mechanism for locking the second handle to the first handle at a desired angular position.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

The acetabular cup inserting instrument 10 of the present invention includes a first elongated handle 12 and a second elongated handle 14 extending from first handle 12. Second handle 14 can be rotated 360° degrees about the longitudinal axis of first handle 12. Second handle 14 may be selectively rotated to a desired position with respect to first handle 12. Likewise, first handle 12 may be rotated relative to second handle 14.

Figure 1:
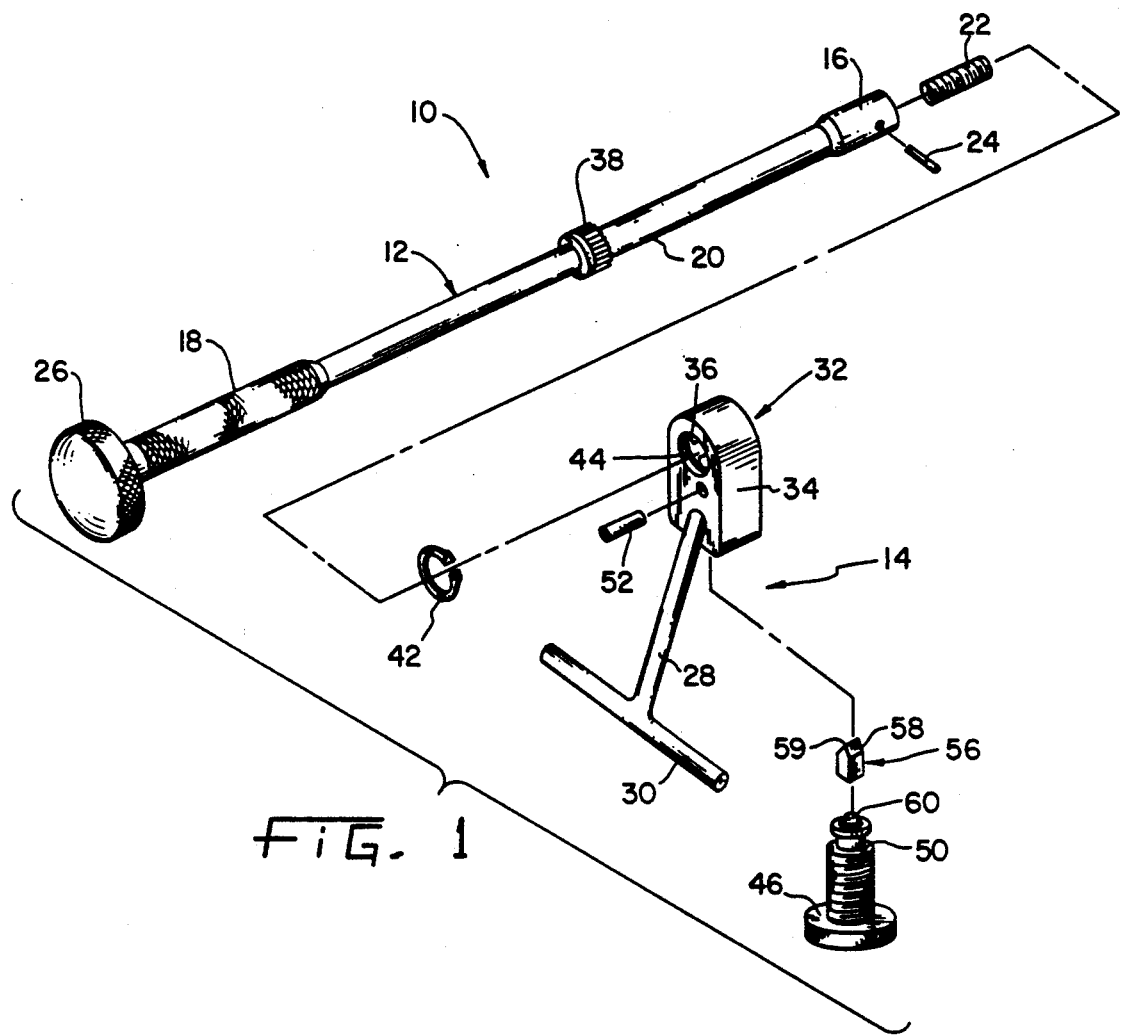
FIG. 1 is an exploded view of the acetabular cup inserting instrument of the present invention.

First handle 12 includes a distal end 16, proximal end 18 and an interconnecting intermediate section 20 therebetween. Distal end 16 includes a means for engaging an acetabular cup (not shown) that securely holds and properly positions the cup. The means for engaging a cup, such as a threaded stud 22, extends from distal end 16 of first handle 12. As shown in FIG. 1, a locking pin 24 may be inserted into holes in first handle 12 and through threaded stud 22 to prevent rotation of stud 22 relative to first handle 12.

Threaded stud 22 engages a corresponding threaded polar hole in an acetabular cup (not shown). It is understood that the instrument 10 of this invention may utilize any suitable acetabular cup engaging means for securing instrument 10 to an acetabular cup, such as an expanding collet, for example.

First handle 12 is provided with enlarged head 26 which may be welded to proximal end 18. Enlarged head or knob 26 facilitates the driving of the acetabular cup. Also, proximal end 18 and Knob 26 may include a knurled surface as shown in FIGS. 1 and 2 to assist in better gripping of instrument 10.

Figure 2:
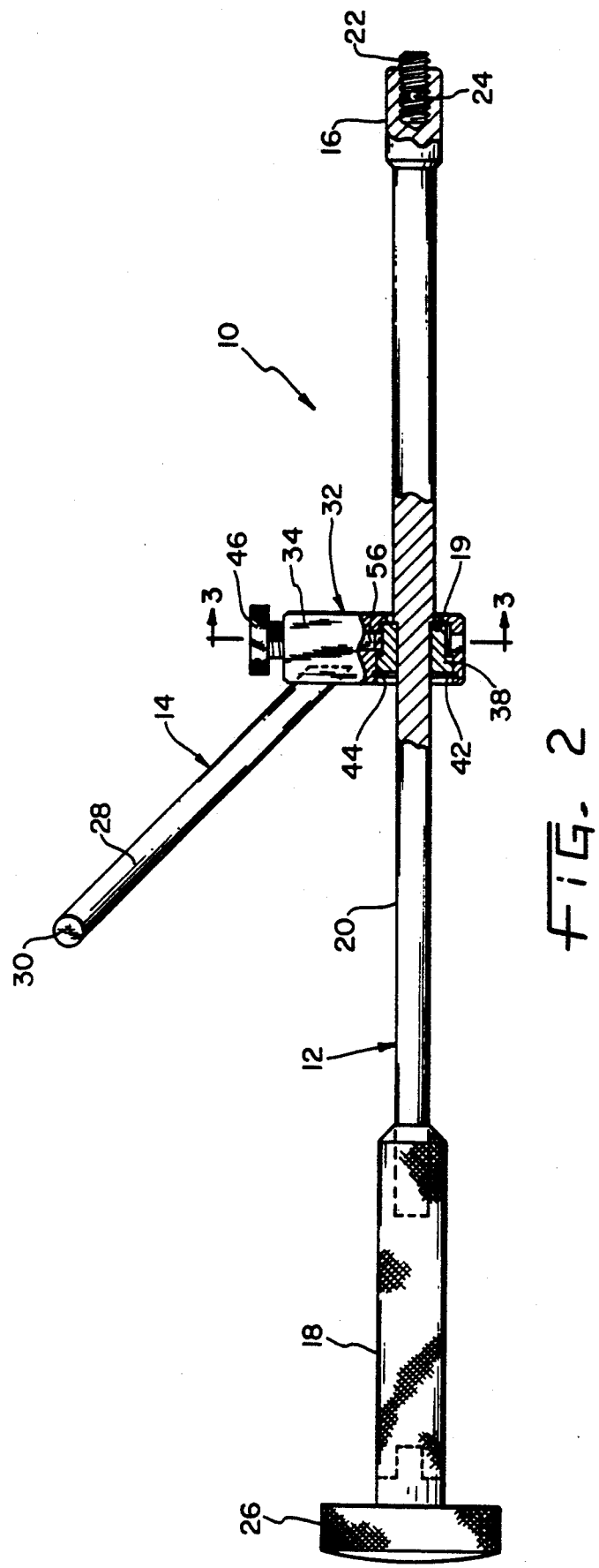
FIG. 2 is a partial sectional side view of the assembled instrument of FIG. 1.

Second handle 14 extends from first handle 12 toward the proximal end 18 at an angle of approximately 45° as shown in FIG. 2. Second handle 14 includes a main alignment arm extension 28 with a cross bar 30 to form a T-shaped handle. A sighting means (not shown), as is known in the art, may be attached to extension 28 to assist in cup placement. Second handle 14 further includes a ratchet mechanism 32 adapted to fit about first handle 12 for interconnecting second handle 14 to first handle 12. Ratchet mechanism 32, which is part of second handle 14, is rotatable 360° about first handle 12.

Ratchet mechanism 32 of the present invention includes a housing 34 having a through-hole 36. First handle 12 interfits through hole 36 so that housing 34 may be preferably located on intermediate section 20. As shown in FIG. 2, the diameter of distal portion of intermediate section 20 is greater than that of the proximal portion forming a shoulder 19. Attached to intermediate section 20 is a notched sleeve member 38 having notches or grooves 40. Notched member 38 is preferably welded to intermediate section 20, abutting shoulder 19. A retainer means, such as retainer washer 42 in the form of a snap ring, for example, is secured against notched member 38 and to housing 34 to assure that ratchet mechanism 32 does not slide axially on first handle 12 after it has been attached. Alternatively, other means may be employed to prevent axial movement of second handle 14 on first handle 12. Retainer washer 42 operates by interfitting within a recess 44 in housing 34. This interfitting connection permits housing 34 to rotate about first handle 12 without moving axially.

Figure 3:
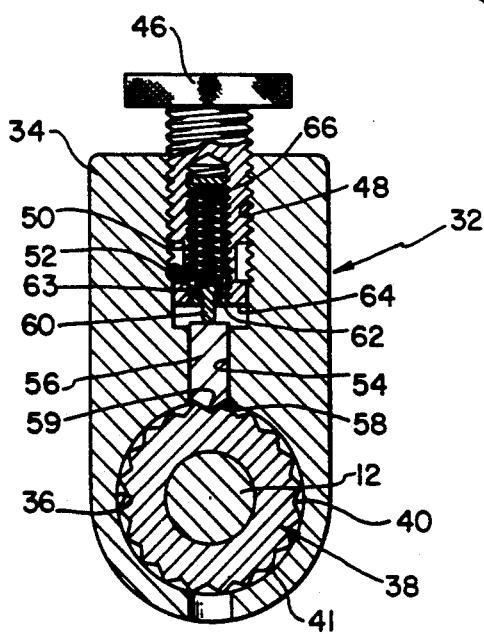
FIG. 3 is a cross sectional view of the instrument taken along line 3—3 of FIG. 2.

The ratcheting or clutch mechanism 32 is controlled by control knob 46 which is threaded for rotation through a threaded hole 48 in housing 34 (see FIG. 3). Control knob 46 includes a circumferential groove 50 that engages a locking cross pin 52. Cross pin 52 is inserted into housing 34 and prohibits removal of control knob 46 from threaded hole 48 yet allows a limited range of travel of knob 46. Threaded hole 48 joins a bore 54 that opens into hole 36.

Within port 54 is a slidable pawl or detent 56 having an engagement surface 58 and point 59 that mechanically and frictionally engages notched member 38 on first handle 12.

Located within control knob 46 is a biased plunger 60, that continuously biases pawl 56 into engagement with grooved portion 40. The limited range of travel of knob 46 enables the plunger 60 to always be in biased engagement with the pawl 56 to some degree. Plunger 60, as shown in FIG. 3, is retained within control knob 46 by a plunger retainer 62 threaded into bore 63 of control knob 46. A biasing means such as a spring 66 is located behind plunger 60 to bias plunger 60 toward pawl 56. The biasing means allows second handle 14 to be located in any position and released without gravity causing second handle 14 to swing freely about first handle 12. The bias of spring 66 against plunger 60, which bias is translated to pawl 56, can be adjusted by rotating knob 46 into or out of housing 34.

Notched member 38, as shown in FIG. 3, includes a plurality of axially extending grooves or notches 40 and projections 41 that are engaged by pawl 56. Preferably the cross sectional angle of notches 40 is approximately 120°, although this angle may vary from 90° to 150° as desired. Pawl 56 preferably includes a point 59 with surfaces 58 that correspond to the mitered angle of notches 40. Additionally, notches 40 may be formed directly on first handle 12 thereby eliminating the need for notched member 38.

The notches 40 are uniformly circumferentially spaced as shown in FIG. 3 to enable pawl 56, and therefore ratchet mechanism 32, to engage at any selected angular orientation about the longitudinal axis of first handle 12. Pawl 56 positively engages notches 40 on member 38 as second handle 14 is rotated about first handle 12 so that relative rotation between handles 12 and 14 can be accomplished smoothly and without any erratic movement. This enables the second handle to be yieldably retained at a desired angular position relative to first handle 12, yet easily moved when the rotation force applied thereto overcomes the mechanical and frictional engagement between pawl 56 and notched member 38.

While the preferred embodiment of the present invention, as disclosed herein, enables the second handle 14 to ratchet in either direction about the first handle 12, it is understood that the ratchet mechanism of the invention may be designed with other variations, such as to ratchet in only a single direction (not shown), instead of the preferred ratcheting mechanism shown.

Additionally, engagement surface 58 may include a roughened surface or coating to provide increased frictional engagement between pawl 56 and notched member 38. This high friction surface supplements the resistance and control function of pawl 56.

Alternatively, ratchet or clutch mechanism 32 may employ a frictional or clutch pad locking mechanism (not shown) instead of the preferred ratcheting mechanism disclosed.

In order to utilize instrument 10 of the present invention, an acetabular cup (not shown) is attached to distal end 16. In the embodiment illustrated, stud 22 is threaded into a corresponding threaded hole in an acetabular cup.

Ratchet or clutch mechanism 32 may be locked up by rotation of control knob 46. Inward rotation of control knob 46 into housing 34 causes the bottom surface 64 of control knob 46 to move into engagement with pawl 56. When this occurs, pawl 56 is locked from retracting out of notch 40, thereby preventing rotation between second handle 14 and first handle 12. Alternatively, instead of bottom surface 64 engaging and locking pawl 56, the biasing means such as spring 66 may transmit a sufficient force to prevent pawl 56 from retracting and therefore lock second handle 14 in position.

When control knob 46 is backed out of housing 34 and bottom surface 64 is not in engagement with pawl 56, spring biased plunger 60 maintains a yieldable bias against pawl 56. The engagement of pawl 56 with notched member 38 creates a ratchet feel as pawl 56 slides and "clicks" in an even manner over projections 41 when rotated about first handle 12. This ratchet action permits a surgeon to feel the location and movement of second handle 14 as it rotates relative to first handle 12. Once second handle 14 is properly aligned, control knob 46 then can be rotated into locking engagement with pawl 56. It is understood that the instrument of this invention may utilize any suitable control mechanism for regulating the engagement of the pawl.

When second handle 14 is properly aligned and locked into position, the cup can then be properly positioned in the prepared acetabulum. When the acetabular cup is fully seated in the acetabulum, second handle 14, via control knob 46, may be released and instrument 10 is then detached from the acetabular cup (not shown) by unthreading stud 22 from the cup.

It can be readily seen that the present invention provides a second alignment handle 14 that is capable of ratcheting about the axis of first handle 12 in a controlled manner and then selectively locked in a desired position. The invention provides a simple and effective instrument which aids in the proper insertion of acetabular cup implants.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An acetabular cup inserting instrument comprising:
   a first elongated handle having a proximal end, a distal end and an interconnecting intermediate section therebetween, said handle having means on the distal end thereof for holding an acetabular cup,
   a second handle extending from the intermediate section and rotatable about said first handle,
   a ratchet means for yieldably retaining said second handle in a plurality of discrete angular positions as said second handle rotates about said first handle, and wherein said ratchet means includes a housing attached to said second handle, a control knob rotatable within said housing, and a spring biased pawl in said housing biased into engagement with a plurality of notches carried by the first handle, and wherein said pawl is regulated by said control knob, and wherein the housing further includes means for limiting the range of travel of the knob within the housing, thus providing an upper unlocked limit and a lower locked limit, such that when the control knob is rotated to the lower locked limit, the pawl becomes locked to one of said notches, thereby locking said second handle to said first handle at a desired angular position, and when the control knob is rotated to the upper unlocked limit, the pawl remains continuously biased into engagement with the notches of the ratchet means, such that the pawl positively engages the notches of the ratchet means as the second handle is rotated about the first handle, thus enabling the second handle to be yieldably retained at a desired angular position relative to the first handle, yet easily moved when rotation force is applied to the second handle to overcome the mechanical and frictional engagement between the pawl and the notches.

2. The instrument of claim 1 wherein said ratchet means is bi-directional so that said second handle can be rotated in two directions.

3. The instrument of claim 1 wherein said notches are disposed circumferentially on said first handle.

4. The instrument of claim 1 wherein the control knob adjustably compresses said spring of said spring biased pawl to thereby adjust the engagement of said pawl and notches.

5. The instrument of claim 1 wherein said control knob is threadedly connected to said housing.

6. The instrument of claim 1 wherein the control knob includes a circumferential groove that engages a locking cross pin which is inserted into the housing and prohibits removal of the control knob from the housing and comprises the means for limiting the range of travel of the control knob within the housing.

* * * * *